(12) United States Patent
Nakada et al.

(10) Patent No.: US 7,503,512 B2
(45) Date of Patent: Mar. 17, 2009

(54) ELECTROSTATIC ATOMIZER AND AIR PURIFIER USING THE SAME

(75) Inventors: Takayuki Nakada, Hikone (JP); Hiroshi Suda, Takatsuki (JP); Tomonori Tanaka, Kasugai (JP); Tomohiro Yamaguchi, Yasu (JP)

(73) Assignee: Matsushita Electric Works, Ltd., Osaka (JP)

( * ) Notice: Subject to any disclaimer, the term of this patent is extended or adjusted under 35 U.S.C. 154(b) by 202 days.

(21) Appl. No.: 10/559,538

(22) PCT Filed: May 26, 2004

(86) PCT No.: PCT/JP2004/007596

§ 371 (c)(1),
(2), (4) Date: Dec. 2, 2005

(87) PCT Pub. No.: WO2004/110641

PCT Pub. Date: Dec. 23, 2004

(65) Prior Publication Data

US 2006/0144971 A1 Jul. 6, 2006

(30) Foreign Application Priority Data

Jun. 4, 2003 (JP) .............................. 2003-160021

(51) Int. Cl.
*B05B 5/00* (2006.01)
(52) U.S. Cl. .................. 239/690.1; 239/690; 96/27; 96/53; 95/71; 261/107
(58) Field of Classification Search .................. 239/34, 239/145, 326, 690, 697, 690.1; 392/337; 96/52, 53; 95/71
See application file for complete search history.

(56) References Cited

U.S. PATENT DOCUMENTS

| 4,380,786 | A | * | 4/1983 | Kelly | .......................... 361/228 |
| 4,979,968 | A | * | 12/1990 | Jido | .............................. 96/27 |
| 5,196,171 | A | * | 3/1993 | Peltier | ......................... 422/121 |
| 5,337,963 | A | | 8/1994 | Noakes | |
| 5,503,335 | A | | 4/1996 | Noakes et al. | |
| 5,914,454 | A | * | 6/1999 | Imbaro et al. | ................... 95/64 |
| 5,992,771 | A | | 11/1999 | Noakes et al. | |

FOREIGN PATENT DOCUMENTS

| EP | 0 486 198 A1 | 5/1992 |
| JP | 62-144774 A | 6/1987 |
| JP | 05-345156 A | 12/1993 |
| JP | 10-151314 A | 6/1998 |

(Continued)

OTHER PUBLICATIONS

International Search Report.

(Continued)

*Primary Examiner*—Dinh Q Nguyen
(74) *Attorney, Agent, or Firm*—Cheng Law Group PLLC

(57) ABSTRACT

A liquid stored in the liquid storing means within a housing is supplied to a carrier. A high voltage applied to a discharge end of the carrier and an opposed electrode to emit tiny ionized liquid particles. At leas part of the liquid storing means is detachable to the housing for easy replenishment of the liquid.

5 Claims, 4 Drawing Sheets

FOREIGN PATENT DOCUMENTS

| | | |
|---|---|---|
| JP | 10-506838 A | 7/1998 |
| JP | 10-216561 A | 8/1998 |
| JP | 2001-286546 A | 10/2001 |
| JP | 3260150 B2 | 12/2001 |
| JP | 2002-203657 A | 7/2002 |
| JP | 2003-014261 A | 1/2003 |
| JP | 2003-079714 A | 3/2003 |
| JP | 2003-097829 A | 4/2003 |
| JP | 2003-120972 A | 4/2003 |
| WO | WO-96/10331 A1 | 4/1996 |
| WO | WO-96/11062 A1 | 4/1996 |

OTHER PUBLICATIONS

Notification of Reasons for Refusal for the Application No. 2003-160021 from Japan Patent Office, mailed Mar. 25, 2008.

Supplementary European Search Report for the Application No. EP 04 73 4897 dated Jul. 18, 2008.

Notification of Reasons for Refusal for the Application No. 2003-160021 from Japan Patent Office mailed Aug, 26, 2008.

* cited by examiner

ELECTROSTATIC ATOMIZER AND AIR PURIFIER USING THE SAME

TECHNICAL FIELD

The present invention relates to an electrostatic atomizer for emitting a liquid in the form of tiny ionized particles and an air purifier using the same.

BACKGROUND ART

Japanese Patent Publication 2002-203657 discloses a prior art electrostatically atomizing device. The electrostatically atomizing device includes a nozzle dropping or spraying the water into a discharge compartment, and an electrode opposed to the nozzle. A high voltage is applied between the nozzle and the electrode to emit the positively charged water particles from the tip of the nozzle. The water is supplied from a container mounted outside of the discharge compartment. In order to keep the electrostatic atomization over a long period of use, the water has to be regularly replenished to the container, rendering the maintenance annoyance.

DISCLOSURE OF THE INVENTION

The present invention has been achieved to overcome the above problem, and to provide an electrostatically atomizing device and an air purifier using the same which is capable of maintaining stable electrostatic atomization over a long period of use.

The atomizing device in accordance with the present invention includes a carrier carrying the liquid to be atomized, and a liquid storing means storing a volume of the liquid. The carrier is configured to have a liquid collecting end and a discharge end opposite thereto, the liquid collecting end being immersed in the liquid for feeding the liquid to the discharge end. The device includes a first electrode for electrically charging the liquid, and a second electrode opposite to the discharge end, and a voltage source. The voltage source applies a high voltage between the first and second electrodes so as to charge the liquid at the discharge end, thereby discharging the liquid in the form of tiny ionized particles. The liquid storing means is accommodated within a housing together with the carrier, the first and second electrodes, and the voltage source. The feature of the present invention resides in that at least a part of the liquid storing means is detachable to the housing. Thus, the part of the liquid storing means detachable to the housing can be utilized to replenish the liquid without difficulty.

In a preferred embodiment, the liquid storing means is composed of a reservoir mounted within the housing, and a replenishing tank supplying the liquid into the reservoir. The replenishing tank is detachable to the reservoir and is utilized for easy replenishing of the liquid.

Preferably, the reservoir, the carrier, the first electrode, the second electrode, and the replenishing tank are accommodated within a recess formed in the housing. The housing has a lid covering the recess, and a switch is provided to stop applying the high voltage from the voltage source upon opening of the lid. Thus, while replenishing the liquid with the lid opened, the high voltage is not applied to the liquid in the reservoir. Consequently, when the liquid or the electrodes are touched by mistake, the human body can be protected from the high voltage, assuring safe replenishment of the liquid.

In a preferred embodiment, the first and second electrodes are detachably connected respectively to first and second contacts which are accommodated within the housing together with the voltage source. The carrier, the first and second electrodes are accommodated together with the reservoir within a casing which is detachable to the housing. Thus, when the reservoir and the carrier are required to be cleaned, the casing is detached from the housing to make required treatment.

In this case, it is preferred that the housing includes a recess for accommodating the casing and a lid is provided to cover the recess, and that a switch is provided to stop applying the high voltage from the voltage source upon opening of the lid. The recess is preferably is sealed from the interior of the housing to avoid the leakage of the liquid for protection of the voltage source within the housing from the liquid.

The first and second electrodes are mounted in a barrel together with the carrier. The first and second electrodes are provided respectively with first and second terminals for pressed contact with the first and second contacts of the voltage source. The first and second terminals are preferred to be disposed on opposite sides of the barrel to receive from the first and second contacts respectively with contacting forces that counterbalancing with each other. With the counterbalancing forces, the first and second terminals are brought into firm electrical contact respectively with the first and second contacts, thereby assuring the reliable electrical connection between the voltage source in the housing and the first and second electrodes in the casing, while making the casing detachable to the housing.

The electrostatically atomizing device thus configured is preferably incorporated in an equipment such as an air purifier. The air purifier has a housing equipped with a contaminant trapping filter, and a fan circulating the air through the filter. The atomizing device is disposed in the housing downstream of the fan and the filter. Thus, the tine ionized liquid particles as well as negative ions generated from ionizing needle can be carried on the clean air removed of the contaminants through the filter so as to be spread into a room space, giving deodorant effect and/or other environment improving effect of the particles over a wide space of the room.

These and still other objects and advantageous features will become apparent from the detailed explanation of the preferred embodiment when taken in conjunction with the drawings.

BEST MODE FOR CARRYING OUT THE INVENTION

Figure 1:
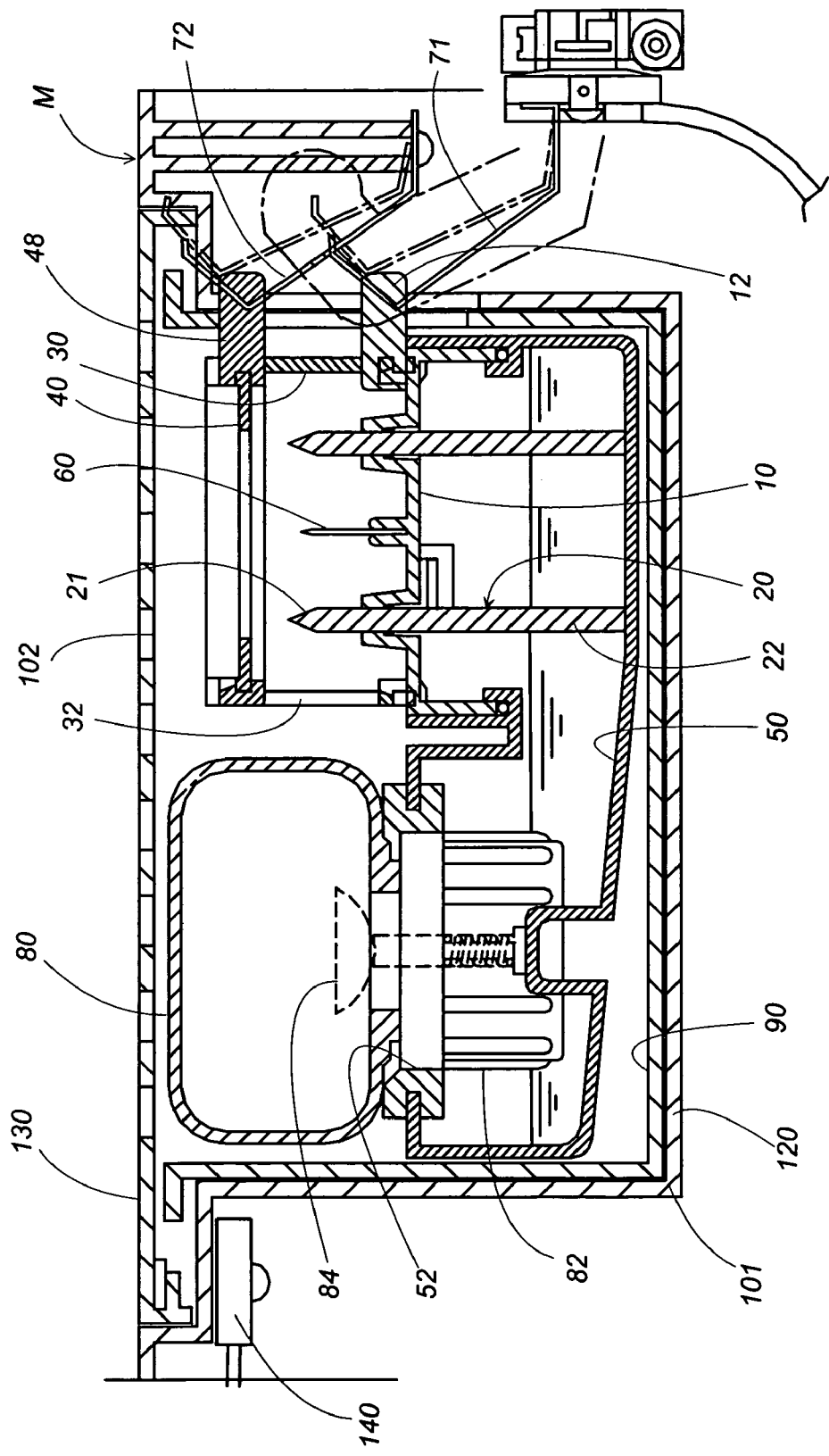
FIG. 1 is a vertical section of an electrostatically atomizing device in accordance with one embodiment of the present invention.
Figure 2:
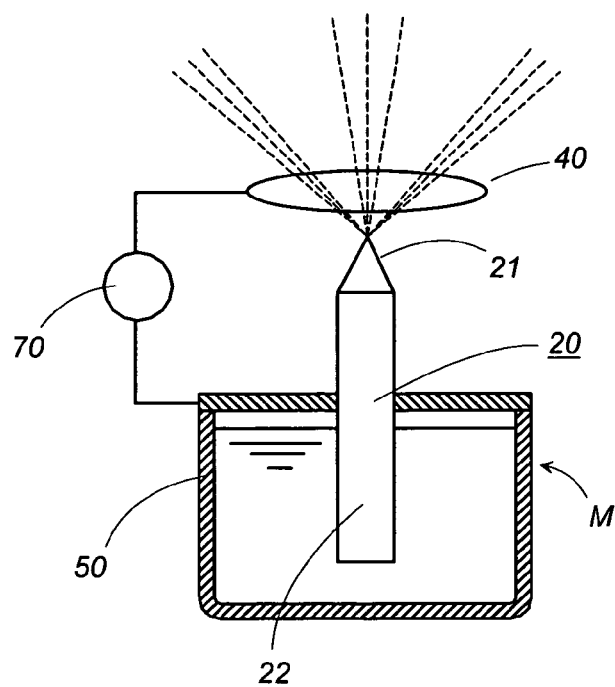
FIG. 2 is a schematic view illustrating the operation of the above device.
Figure 3:
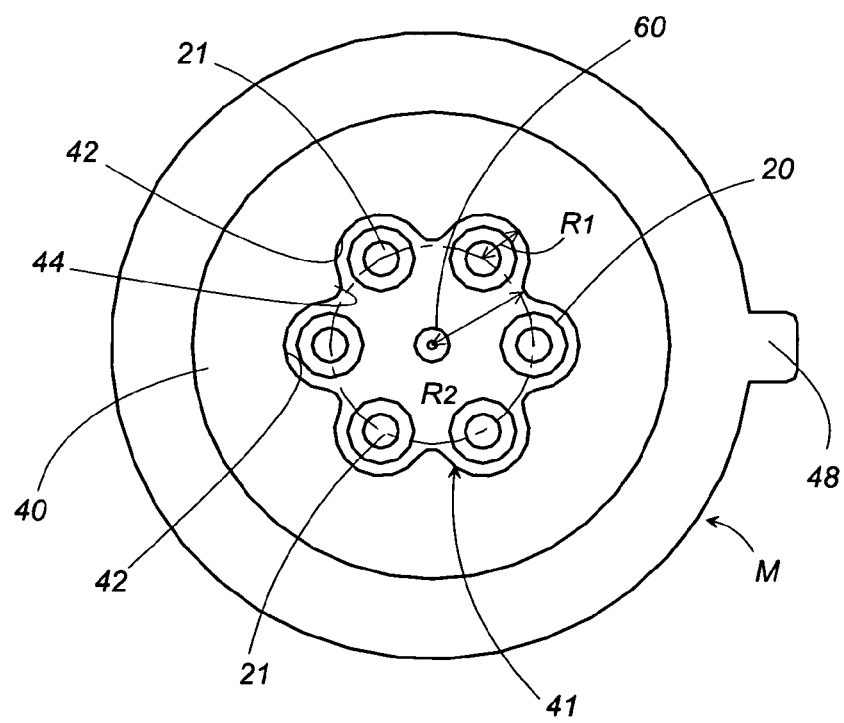
FIG. 3 is a top view of an electrode plate utilized in the above device.
Figure 4:
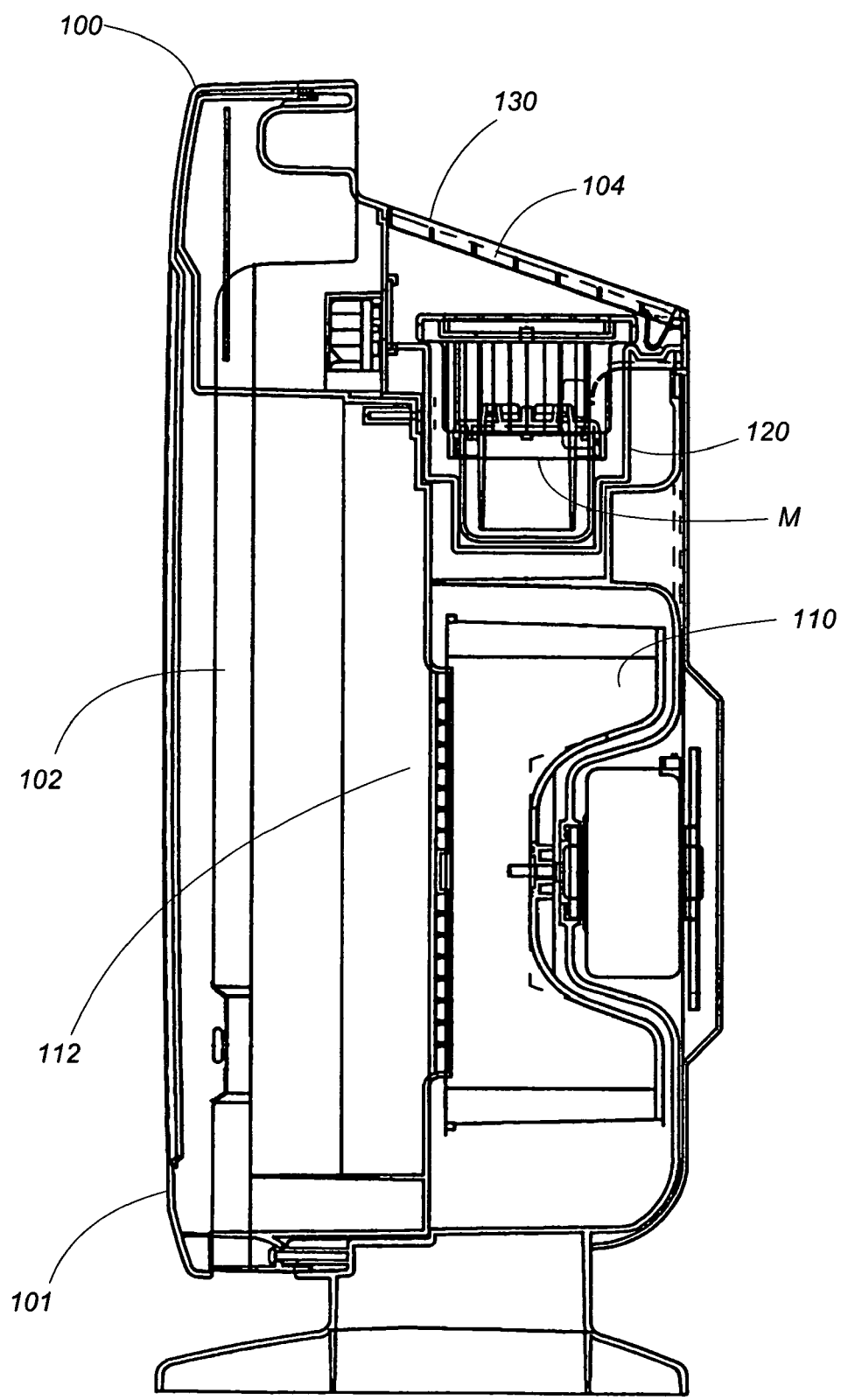
FIG. 4 is a cross-section of an air purifier incorporating the above device.

An electrostatically atomizing device M in accordance with one embodiment of the present invention is configured to ionize particulate water, for example, so as to generate ionized water particles of a nanometer. As shown in FIG. 1, the atomizing unit M includes a base 10 supporting a plurality of capillary carriers 20, a barrel 30 surrounding the top of the base 10, an electrode plate 40 fitted in the top opening of the barrel 30, and a reservoir 50 attached to the lower side of the base 10. The base 10 and the reservoir 50 are accommodated within a casing 90 together with a replenishing tank 80 detachable to the reservoir 50. The casing 90 is accommodated within a recess 120 that is formed in a housing 101 of an air purifier 100, as shown in FIG. 4. In the present embodiment, the reservoir 50 and the replenishing tank 80 are cooperative to define a liquid storing means for storing the liquid to be supplied to capillary carriers 20. The recess 120 is sealed from the interior of the housing 101 to protect the high voltage source 70 from the water, in case the water leaks in the recess 102. As shown in FIG. 1, the liquid storing means defined by the reservoir 50 and the replenishing tank 80 is accommodated within the housing (101) together with the capillary carriers 20.

Each of the capillary carriers 20 is made from porous ceramic and shaped into a porous bar having a diameter of about 5 mm and a length of about 70 mm, and extending through the base 10. The carrier 20 is formed with a discharge end 21 at its pointed end of a portion projecting on top of the base 10, and with a liquid collecting end 22 at its portion projecting on the underside of the base 10. The liquid collecting end 22 is immersed in the water in the reservoir 50 to suck up the water and feed it to the discharge end 21 by the capillary action. The base 10 is made of an electrically conductive plastic material and acts as a first electrode giving negative electrical potential to each capillary carrier 20. For this purpose, the base 10 is formed at its periphery with a first terminal 12 for connection with negative side of the high voltage source 70.

The high voltage source 70 is configured to apply the high voltage having an electric field strength of 500 V/mm, for example, between the base 10 and the electrode plate 40, developing an electrostatic atomization between the discharge end 21 at the distal end of the capillary carrier 20 and the electrode plate 40 defining the second electrode opposing the discharge end, such that tiny ionized water particles are emitted from the discharge end 21 towards the electrode plate 40. That is, the high voltage induces Rayleigh disintegration of the water being emitted from the discharge end, thereby generating negatively-charged water particles and emitting the mist of the tiny ionized water particles. In the present embodiment, the electrode plate 40 is connected to a ground potential so as to give a predetermined voltage difference relative to the negative potential given to the base 10. The high voltage source 70 applies a continuous or pulses of the high voltage between the electrode plate 40 and the base 10. The high voltage source 70 can be accommodated within the housing (101) together with the base 10 and the electrode plate 40.

The electrode plate 40 is molded from an electrically conductive resin and shaped to have a circular outer periphery with a center opening having a star-shaped opening circumference 41. The opening circumference is held in closely opposed relation to the discharge end 21 of each carrier 20 to develop a discharge between the opening circumference 41 and the discharge ends 21. The electrode plate 40 is formed at its periphery with a second terminal 48 for connection with the positive side of the high voltage source 70. The first terminal 12 and the second terminal 48 are configured to come into pressed contact respectively with first and second contacts 71 and 72 that are connected respectively with the positive and negative sides of the voltage source 70. The first and second contacts 71 and 72 can be accommodated within the housing (101) together with the voltage source 70.

The barrel 30 is formed in its outer wall with a plurality of windows 32 through which the air is introduced to make an air flow directed outwardly of the center opening of the electrode plate 40. The negatively ionized tiny water particles generated between the discharge ends 21 and the electrode plate 40 are carried on the air flow so as to be emitted in the form of a mist into a wide space. As shown in FIG. 4, since the electrostatically atomizing device M is incorporated in the air purifier 100, the forced air flow generated at the air purifier 100 is best utilized to scatter the tiny ionized water particles over wide range. The housing 101 of the air purifier 100 has an air inlet 102 and an air outlet 104. A fan 110 and a filter 112 entrapping the dust and other contaminants are accommodated within the housing 101 so as to draw the outside air through the filter 112 and flow the clean air out of the air outlet 104. The electrostatically atomizing device M is disposed adjacent to the air outlet 104 downstream of the filter 112 and the fan 110.

The base 10 supports at its center an ionizing needle 60 which has a pointed tip projecting upwardly of the base in alignment with the discharge ends of the capillary carriers 20 and which is electrically charged to the same potential as the capillary carriers 20. The capillary carriers 20 are evenly spaced in a circle concentric to the ionizing needle 60. The opening circumference 41 of the electrode plate 40, which define the opposed electrode commonly to the capillary carriers 20 and the ionizing needle 60, is defined by a combination of a plurality of curved edges 42. Each of the curved edges is a semi-circular edge about the discharge end 21 of each corresponding capillary carrier 20 leaving a constant distance with the discharge end 21. The adjacent curved edges 42 define therebetween a second edge 44 that is opposed to the ionizing needle 60 to bring about a corona discharge therebetween, thereby negatively charging molecules such as oxygen, oxide, or nitride in the air to generate negatively charged ions, while restraining the generation of ozone. The distance R2 between the second edge and the ionizing needle 60 is made greater than the distance R1 between the first curved edge 42 and the discharge end 21, such that the atomization of the liquid at the discharge end 21 and the generation of the negatively charged ions at the ionizing needle 60 can be done respectively at optimum conditions.

The reservoir 50 is horizontally elongated to provide a connection port 52 which is formed in top of a side extension from the barrel 30 to detachably receive a spout 82 of the replenishing tank 80. The spout 84 includes a valve 84 which opens in response to the insertion of the spout 82 into the connection port 52 for replenishing the water from the tank 80 into the reservoir 50.

The base 10 carrying the capillary carriers 20 and the barrel 30 surrounding the top of the base 10 are integrated with the reservoir 50, and are retained together with the replenishing tank 80 within the casing 90. The recess 120 of the housing 101 configured to detachably receive the casing 90 is provided with a lid 130. With the lid 130 being opened, the replenishing tank 80 is attached to or detached from the reservoir 50, in addition to that the casing 90 is attached to or detached from the recess 120. The lid 130 is made of a perforated pate to define the air outlet 104. Disposed around the periphery of the recess 120 is a proximity switch 140 that stops the high voltage source 70 or interrupts the electrical connection from the high voltage source 70 to the first and/or second terminals 71 and 72 in response to the opening of the lid 130. Thus, the high voltage can not be applied to the capillary carriers 20 and the water in contact therewith, assuring safe attachment and detachment of the replenishing tank 80 or the casing 90, or safe inspection of the interior of the device.

Figure 5:
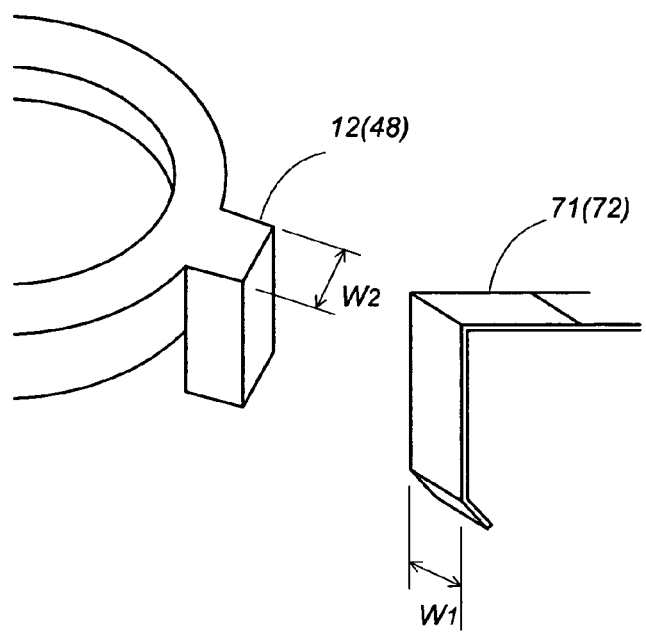
FIG. 5 is an exploded perspective view of a portion of the above device.

The first contact 71 and the second contact 72 are each shaped into a metal spring leaf in order to make the electrical connection respectively with the first terminal 12 and the second terminal 48 by the spring pressure. As shown in FIG. 5, the contacting areas of the first contact 71 and the second contact 72 are each rectangular and has a width (W1) greater than the width (W2) of the first terminal 12 and the second terminal 48. Thus, the first terminal 12 and the second terminal 48 made of the electrically conductive plastic material are prevented from being scraped off by the edge of the spring leaves at the time of attachment or detachment of the atomizing device M, keeping reliable electrical connection.

Each of the capillary carriers 20 is made of the porous ceramic material of particle size of 2 to 500 μm and has a porosity of 10 to 70% to feed the water to the discharge end 21 by the capillary effect using minute paths in the ceramic. The ceramic is selected from one or any combination of alumina, titania, zirconia, silica, and magnesia, and is selected to have a PH at the isoelectric point lower than PH of the water in use. The basis of such selection is related to mineral components such as Mg and Ca possibly contained in the water being utilized. The mineral components contained in the water are refrained from advancing to the discharge end of the capillary carrier 20 and therefore refrained from reacting with $CO_2$ in the air to precipitate as MgO or $CaCO_3$ which would otherwise impede the electrostatic atomization effect. That is, the electroosmotic flow in the capillary carriers 20 can be best utilized so that Mg or Ca ions dispersed in the water is prevented from advancing to the discharge end 21.

Figure 6:
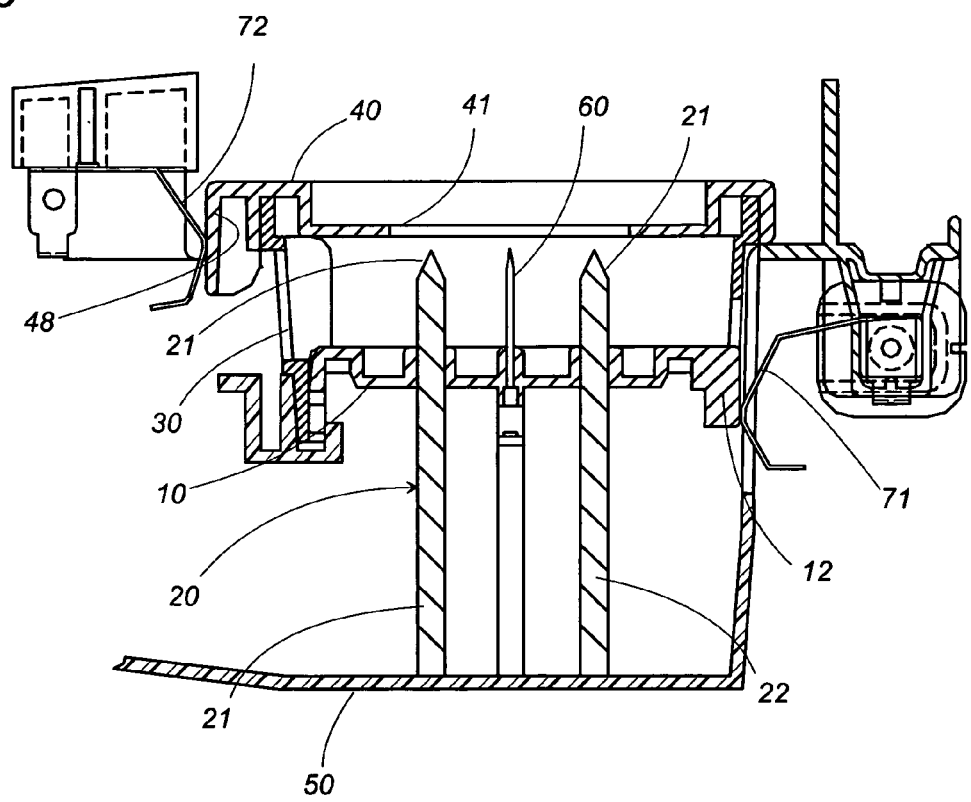
FIG. 6 is a cross-section illustrating an electrostatically atomizing device in accordance with another embodiment of the present invention.

When the mist of the tiny ionized water particles caused by the electrostatic atomization is generated at a rate of 0.02 ml/m within an electric field strength of 500 V/mm or more with the use of the capillary carrier 20 of which tip diameter is 0.5 mm or below, the mist contains the very fine ionized particles having the nanometer particle size of 3 to 100 nm, which react with the oxygen in the air to give the radicals such as hydroxyl radicals, superoxides, nitrogen monoxide radicals, and oxygen radicals. The mist of the tiny ionized water particles, when released into a room, can deodorize substances contained in the air or adhered to the walls. The following are reaction formulas between the radicals and various kinds of odor gases.

ammonia: $2NH_3 + 6.OH \rightarrow N_2 + 6H_2O$ acetaldehyde: $CH_3CHO + 6.OH + O_2 \rightarrow 2CO_2 + 5H_2O$ acetic acid: $CH_3COOH + 4.OH + O_2 \rightarrow 2CO_2 + 4H_2O$ methane gas: $CH_4 + 4.OH + O_2 \rightarrow CO_2 + H_2O$ carbon monoxide: $CO + 2.OH \rightarrow CO_2 + 4H_2O$ nitrogen monoxide: $2NO + 4.OH \rightarrow N_2 + 2O_2 + 2H_2O$ formaldehyde: $HCHO + 4.OH \rightarrow CO_2 + 3H_2O$ FIG. 6 illustrates another embodiment of the present invention which is basically identical to the above embodiment except that the first terminal 12 and the second terminal 48 are disposed on diametrically opposed ends so as to approximately counterbalance the spring forces, one acting from the first contact 71 to the first terminal 12, and the other acting from the second contact 72 to the second terminal 48. Thus, the sufficient contacting pressure can be obtained at the respective connections to make the reliable electrical connection of the high voltage source 70 to the base 10 and the electrode plate 40. The like parts are designated by like reference numerals.

Although the above embodiment is explained with reference to an example in which the water is utilized to generate mist of the tiny ionized water particles, the present invention is not limited to the particular embodiment, and can be applicable to the use of the various liquids other than the water. The available liquid includes the water containing valuable components such as vitamin C, amino acids, a deodorant such as fragrant oil or aromatic, and includes a colloidal solution such as a make-up lotions.

The invention claimed is:

1. An electrostatically atomizing device comprising:

a liquid storing means for storing a volume of liquid;

a carrier having a liquid collecting end and a discharge end opposite of said liquid collecting end, said liquid collecting end being immersed within said liquid in said reservoir for collecting and feeding the liquid through said carrier to said discharge end, a first electrode electrically charging said liquid, a second electrode opposed to said discharge end, a voltage source applying a voltage across said first and second electrodes to thereby electrostatically charge the liquid at said discharge end and emitting the said liquid in the form of tiny ionized particles, said liquid storing means being accommodated within a housing together with said carrier, said first electrode, said second electrode, and said voltage source, and at least a part of said liquid storing means being detachable to said housing, wherein said liquid storing means comprises a reservoir accommodated within said housing and a replenishing tank for supplying the liquid to said reservoir, said replenishing tank being detachable to said reservoir, and wherein said housing is provided with a recess for accommodating therein said reservoir, said carrier, said first electrode, said second electrode, and said replenishing tank, said recess being covered with a lid, said device including a switch that disables said voltage source upon opening of said lid.

2. An electrostatically atomizing device comprising:

a liquid storing means for storing a volume of liquid;

a carrier having a liquid collecting end and a discharge end opposite of said liquid collecting end, said liquid collecting end being immersed within said liquid in said reservoir for collecting and feeding the liquid through said carrier to said discharge end, a first electrode electrically charging said liquid, a second electrode opposed to said discharge end, a voltage source applying a voltage across said first and second electrodes to thereby electrostatically charge the liquid at said discharge end and emitting the said liquid in the form of tiny ionized particles, said liquid storing means being accommodated within a housing together with said carrier, said first electrode, sad second electrode, and said voltage source, and at least a part of said liquid storing means being detachable to said housing, wherein said liquid storing means comprises a reservoir accommodated within said housing and a replenishing tank for supplying the liquid to said reservoir, said replenishing tank being detachable to said reservoir, and wherein said voltage source is accommodated within said housing together with a first contact and a second contact which are detachable to said first and second electrodes respectively for electrically connection thereto, said reservoir being accommodated within a casing together with said carrier, said first electrode, and said second electrodes, said casing being detachable to said housing.

3. The device as set forth in claim 2, wherein said housing has a recess for receiving therein said casing and a lid covering said recess, said device including a switch that disables said voltage source upon opening of said lid.

4. The device in claim 3, wherein said recess being sealed from the interior of said housing where said voltage source is accommodated.

5. The device as set forth in claim 2, wherein said carrier is mounted to a barrel together with said first and second electrodes, said first and second electrodes having first and second terminals for pressed contact respectively with said first and second contacts of said voltage source, said first and second terminals being disposed on opposite of said barrel to receive from said first and contacts respectively contacting forces that counterbalances with each other.

* * * * *